United States Patent
Agostini et al.

(10) Patent No.: US 6,780,402 B1
(45) Date of Patent: *Aug. 24, 2004

(54) MAKE-UP COMPOSITIONS CONTAINING PHENYLATED SILICONE OILS, WHICH ARE RESISTANT TO TRANSFER AND MIGRATION

(75) Inventors: Isabelle Agostini, Chatenay Malabry (FR); François Pradier, Fontenay Aux Roses (FR); Pascal Arnaud, Creteil (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/643,360

(22) Filed: May 6, 1996

(30) Foreign Application Priority Data

Jul. 28, 1995 (FR) .......................................... 95 09254

(51) Int. Cl.$^7$ ..................... A61K 7/027; A61K 47/32
(52) U.S. Cl. .................... 424/64; 424/63; 424/DIG. 5; 514/772.4
(58) Field of Search .............................. 424/40, 63, 64, 424/DIG. 5; 514/947, 969, 772.4

(56) References Cited

U.S. PATENT DOCUMENTS

| | | | |
|---|---|---|---|
| 3,641,239 A | 2/1972 | Mohrlok et al. ............. | 424/614 |
| 3,857,805 A | 12/1974 | Prickril ....................... | 260/28.5 |
| 4,578,266 A | 3/1986 | Tietjen et al. ................. | 424/63 |
| 4,725,658 A | 2/1988 | Thayer et al. ................ | 528/15 |
| 4,919,934 A | 4/1990 | Deckner et al. | |
| 4,980,440 A | 12/1990 | Kendziorski et al. ......... | 528/15 |
| 4,990,561 A | 2/1991 | Yoshioka | |
| 5,051,489 A | 9/1991 | O'Lenick, Jr. ................ | 528/26 |
| 5,061,481 A | 10/1991 | Suzuki et al. ................. | 424/63 |
| 5,066,485 A | 11/1991 | Brieva et al. | |
| 5,087,443 A | 2/1992 | Chizat et al. .................. | 424/47 |
| 5,118,507 A | 6/1992 | Clement ...................... | 441/401 |
| 5,143,722 A | 9/1992 | Hollenberg et al. | |
| 5,210,251 A | 5/1993 | Ohashi et al. .............. | 556/437 |
| 5,254,542 A | 10/1993 | Sakuta et al. | |
| 5,266,321 A | 11/1993 | Shukuzaki et al. .......... | 424/401 |
| 5,288,482 A | 2/1994 | Krzysik ....................... | 424/64 |
| 5,302,380 A * | 4/1994 | Castrogiovanni ............. | 424/63 |
| 5,334,372 A | 8/1994 | Kawamata et al. ...... | 424/78.03 |
| 5,334,737 A | 8/1994 | Thimineur et al. .......... | 556/440 |
| 5,422,412 A | 6/1995 | Morita et al. ................. | 528/25 |
| 5,505,937 A | 4/1996 | Castrogiovanni et al. ..... | 424/64 |
| 5,531,986 A * | 7/1996 | Shevada et al. | |
| 5,556,613 A * | 9/1996 | Arnaud et al. | |
| 5,567,426 A * | 10/1996 | Nadaud et al. .......... | 424/70.12 |
| 5,936,002 A * | 8/1999 | Agostini | |
| 5,965,148 A * | 10/1999 | Agostini et al. | |
| 6,024,969 A * | 2/2000 | Agostini et al. | |
| 6,136,332 A * | 10/2000 | Grollier et al. | |

FOREIGN PATENT DOCUMENTS

| | | |
|---|---|---|
| CA | 2141124 | 7/1995 |
| EP | 0 133 963 A2 | 3/1985 |
| EP | 0 133 964 A2 | 3/1985 |
| EP | 0 197 485 A3 | 10/1986 |
| EP | 0 268 950 A2 | 6/1988 |
| EP | 0 268 950 A3 | 6/1988 |
| EP | 0 310 252 A1 | 4/1989 |
| EP | 0 602 905 A2 | 6/1994 |
| FR | 2 646 346 | 11/1990 |
| FR | WO93/17660 | 9/1993 |
| JP | 61-65808 | 4/1986 |
| JP | 61-65809 | 4/1986 |
| JP | 61-66752 | 4/1986 |
| JP | 61-113646 | 5/1986 |
| JP | 62-45656 | 2/1987 |
| JP | 62-298519 | 12/1987 |
| JP | 1-207354 | 8/1989 |
| JP | 6-48928 | 2/1994 |
| JP | 61-65809 | 4/1996 |

OTHER PUBLICATIONS

New Product Information, Dow Corning 244, 245, 344, 345, 1463, and 200 (0,65 mm$^2$/s) Volatile Silicone Fluids, Document Data Sheet 22–1253–04, Aug. 1989.
Information about Cosmetic Ingredients, Dow Corning, 200 fluid, Bulletin: 22–069–02, dated Dec. 1972.
Information sur les silicone pour produits cosmetiques, Dow Corning, Fluid DC 556, cosmetique, Bulletin 22–242–02–80, 1980.
Wacker Silicone, Belsil Phenyldimethicone–90k München, Jan. 1990.
Fluids, Exxon Chemical, Isopar L, 93, Sep. 27, 1993.
Declaration de Pascal Arnaud, Feb. 4, 1999.
Information about Cosmetic Ingredients, Dow Corning, 200 fluid, Form No. 22–2290–79, 1979.
Décision intermédiaire en procédure d'opposition (Articles 102(3) et 106(3) CBE).
Japanese Abstract of 61–65809.
Derwent Info. 1998 of JP 6–48928.
EP–A–0 268 950 Application (in French).
European Patent Application 0756 864 (in Germany).
International Cosmetic Ingredient Dictionary and Handbook, 7$^{th}$ Edition, 1997, vol. 1, p. 1033.
Japanese Patent Application Sho 62–298519.
Japanese Abstract of 62–298519.
Japanese Patent Application Sho 59–187138.
Japanese Abstract of 61–65808.
Official Gazette, Japanese Application No. 84–187139.
Abstract of Japanese 61–65809.
Japanese Patent Application No. Hei 3–173372.
DC 943 Formulation Sheet No. 22–180, Aug. 1989, "Luxury Bath Oil".

* cited by examiner

Primary Examiner—Edward J. Webman
(74) Attorney, Agent, or Firm—Burns, Doane, Swecker & Mathis, L.L.P.

(57) ABSTRACT

This application concerns the use of the combination of a volatile oil and a phenylated silicone oil in a composition containing a fatty phase.

The invention also relates to a composition containing, in a fatty phase, a volatile oil, a phenylated silicone oil, and less than 20% by weight of a non-volatile hydrocarbonic oil.

25 Claims, No Drawings

MAKE-UP COMPOSITIONS CONTAINING PHENYLATED SILICONE OILS, WHICH ARE RESISTANT TO TRANSFER AND MIGRATION

The present invention concerns a composition, in particular a cosmetic composition capable of being applied on the skin and/or lips, and, in particular, an anhydrous composition for the care and/or make-up of the skin, and/or lips, especially a lipstick in stick form or a make-up foundation.

Lipstick and make-up foundation compositions normally contain fatty substances such as oils, viscous compounds and waxes, as well as particulate phase usually composed of fillers and pigments. When applied to the skin or lips, these compounds have the disadvantage of being transferred, that is, of forming a deposit, at least in part, while leaving a trace on objects with which they come into contact, in particular, a glass, a cup, a piece of clothing or the skin. Consequently, there remains on the skin or lips a reduced film which requires the periodic re-application of the make-up foundation or lipstick composition.

Furthermore, the appearance of unacceptable traces on clothing and, most especially, on the necks of blouses, may dissuade some women from using this type of make-up.

Another disadvantage of these compositions lies in the problem of migration. Indeed, it has been observed that some foundation compositions tended to spread inside wrinkles in the skin, that some lipstick compositions traveled in the small wrinkles surrounding the lips, while eye-shadows tended to spread in the folds of the eyelids. In the case of eye-shadows, the appearance of lines in the make-up, caused by movements of the eyelids, were also noted. All of these phenomena produced an unaesthetic effect which the consumer quite obviously wished to avoid.

For several years, many cosmeticians have been interested in lipsticks, and, more recently, make-up foundation compositions, that "did not transfer." Thus, Patent Application No. JP-A-61-65809 disclosed "transferless" lipstick compositions containing 1 to 70% by weight of a liquid silicone resin incorporating repeating silicate patterns (or having a three-dimensional lattice) comprising alkylated suspended chains of 1 to 6 atoms of carbon or phenylated chains, 10 to 98% by weight of a volatile silicone oil having a cyclic Si—O chain and containing methyl radicals, and pulverulent fillers. These compositions, although highly satisfactory as regards the lack of transference, had the disadvantage of being in liquid form and thus inconvenient to use, or, at the very least, of being far removed from the conventional idea of a lipstick, thereby limiting the number of women prepared to use this type of lipstick. In addition, the film produced on the lips after evaporation of the silicone oil had the disadvantage of becoming uncomfortable over time (sensation of drying and tugging, thus dissuading still other women from using this type of lipstick). To enhance the comfort given by this type of composition, non-volatile oils, whether or not they contained silicone, could be added; however, in this case the "transferless" property is lost. Moreover, these compositions take a long time to dry: that is, the lack of transfer appears only after several minutes.

More recently, Patent Application No. EP-A-602905 disclosed "transferless" lipsticks containing a volatile cyclic or linear silicone containing suspended methylated chains and a silicone resin incorporating a suspended esterified chain having at least 12 atoms of carbon. The lipstick film still possesses the problem of being uncomfortable when applied and, most notably, of being too dry.

The invention in question is intended to propose a composition, in particular an anhydrous composition, for skin care or make-up making it possible to remedy these difficulties, while, in particular, allowing the production of a film that does not transfer or migrate and that does not stain an object with which it comes into in contact, while exhibiting improved cosmetic properties as compared with the properties of "transferless" products according to prior art, in particular smooth sliding, the absence of tugging, and the lack of drying of the lips.

Accordingly, the object of the invention is the use of the combination of a volatile oil and a silicone-containing phenylated oil in a composition containing a fatty phase, in order to reduce transfer and/or migration and/or to improve the holding power of this composition.

Another object of the invention is a composition containing, in a fatty phase, a volatile oil, a silicone-containing phenylated oil, and less than 20% by weight of a non-volatile hydrocarbonic oil, e.g., a foundation product.

The invention encompasses compositions to be applied to the skin, the semi-mucous membranes, e.g., the lips, and/or the mucous membranes, e.g., the internal areas of the eyelids, and, in particular, not only to lip make-up but also to lip-care products and to skin and rouge make-up and care products such as foundations. In fact, facial make-up products possess the same problems of "transfer" to an object as do lipsticks.

The composition according to the invention may exist in solid form, e.g., as a stick. Furthermore, it yields a homogeneous film that is easily applied and spreads smoothly and uniformly. The film produced also has a light texture and remains comfortable and moist, and can be worn throughout the day.

The invention composition thus comprises a volatile oil which can be chosen, in particular, from hydrocarbonic or silicone-containing oils, whether cyclic or linear, either alone or in mixtures. The term "volatile oil" in this description signifies any oil that can evaporate on contact with the skin. Preferably, use is made of oils whose flash point is sufficiently high to allow the use of these oils in formulations, and low enough to obtain the desired evanescent effect. Oils having a flash point of approximately 40–100° C. are preferably used.

Usable volatile silicone oils include cyclotetradimethylsiloxane, cyclopentadimethylsiloxane, cyclohexadimethylsiloxane, and methylhexyldimethylsiloxane. Among the volatile hydrocarbonic oils, isoparaffins may be mentioned.

The composition according to the invention may contain 8–70% by weight, and preferably 30–60%, volatile oils in relation to the total weight of the composition.

The composition according to the invention also contains at least one phenylated silicone oil. This oil may be a polyphenylmethylsiloxane or a phenyltrimethicone, or a mixture of different phenylated silicone oils, and, in particular, it may correspond to the following formula:

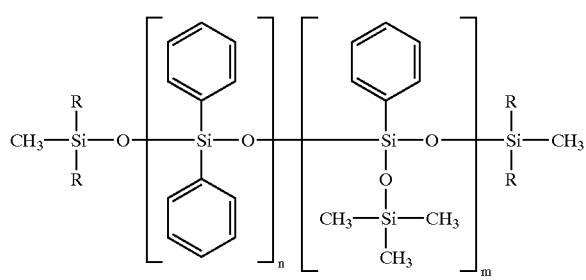

(I)

where:
R is an alkyl radical at C1–C30, an aryl radical, or an aralkyl radical
n is a whole number between 0 and 100,
m is a whole number between 0 and 100, provided that the sum m+n is between 1 and 100.

Preferably, R is a methyl, ethyl, propyl, isopropyl, decyl, dodecyl, or octadecyl radical, or a phenyl, tolyl, benzyl, or phenethyl radical.

Among these phenylated oils, mention may be made of Belsil PDM1000 oil from Wacker, DC556 and SF558 oils made by Dow Corning, Abil AV8853 oil made by Goldschmidt, and Silbione 70633V30 oil manufactured by Rhône Poulenc.

The composition according to the invention may contain 1–35% by weight, and preferably 20–30% by weight, phenylated silicone oils.

In addition to the oils cited above, the fatty phase may contain the fatty substances normally used in the contemplated scope of application. These substances include silicone-containing fatty substances such as oils, viscous fatty substances, silicone waxes, and non-silicone-containing fatty substances such as oils, viscous substances, and vegetable, mineral, animal, and/or synthetic waxes.

Silicone-containing fatty substances include polydimethylsiloxanes (PDMS) and alkyldimethicones, as well as silicones modified by potentially fluorinated aliphatic and/or aromatic groups or by functional groups, such as hydroxyl groups, thiols, and amines.

Among non-silicone-containing fatty substances, mention may be made of paraffin, vaseline, perhydrosqualene, arara oil, sweet almond oil, calophyllum oil, palm oil, castor oil, avocado oil, jojoba oil, olive oil, or cereal gerin oil; esters of fatty acids; alcohols; acetylglycerides; the octanoates, decanoates, and ricinoleates of alcohols and polyalcohols; fatty acid triglycerides; glycerides; concrete hydrogenated oil at 25° C.; lanolines; concrete fatty esters at 25° C.; beeswaxes; vegetable waxes such as carnauba, candellila, urricury, and Japan waxes or cork or sugar cane fiber waxes; mineral waxes, e.g., paraffin and lignite waxes and microcrystalline waxes and ozokerites; synthetic waxes, including polyethylene waxes and waxes produced by Fischer-Tropsch synthesis.

The choice of these fatty substances made by the specialist may be varied, in order to prepare a composition having the desired properties, e.g., consistency and texture.

In particular, the composition according to the invention may contain at least one wax, in order to ensure mechanical strength when the composition is produced in stick form.

When it exists as a flexible paste or molded product, the composition according to the invention contains a smaller quantity of wax, e.g., of approximately 2 to 15% by weight.

In general, the composition may contain 0.5 to 30% by weight of at least one hydrocarbonic and/or silicone wax, and, preferably, 10–20% by weight of hydrocarbonic wax and 0 to 10% by weight silicone wax.

Furthermore, it has been found that the improved staying power of the composition according to the invention and the absence of migration and/or transfer thereof could prove particularly advantageous when the composition contains less than 20% by weight of a non-volatile hydrocarbonic oil, preferably less than 5% by weight, and, in fact, it might contain no non-volatile hydrocarbonic oils at all.

The composition according to the invention may contain a particulate phase normally accounting for 0 to 35% by weight and preferably 5–25% by weight, and this phase may contain the pigments and/or nacres and/or fillers normally used in cosmetic compositions.

The term pigments refers to white or colored mineral or organic particles which are insoluble in wax and volatile silicone and which are intended to color the composition and/or render it opaque. The term fillers refers to colorless or white mineral or synthetic particles, whether lamellate or non-lamellate, intended to impart body or stiffness to the composition. The term nacres refers to iridescent particles rich in lime and produced by certain mollusks in their shell.

The pigments may make up 0 to 15% by weight of the final composition, and preferably from 8 to 10%. They may be white or colored, mineral and/or organic. Among the mineral pigments, mention may be made of titanium, zirconium, or cerium dioxides, as well as zinc, iron, or chrome oxides and ferric blue. Organic pigments include carbon black and barium, strontium, calcium, and aluminum lacquers.

The nacres may make up 0 to 20% by weight of the composition, preferably in a high proportion of approximately 8 to 15% by weight. Usable nacres include mica coated with titanium oxide, iron oxide, natural pigment or bismuth oxychloride, as well as colored mica titanium.

The fillers, which may compose 0 to 30% by weight, and preferably 5 to 15%, of the composition may be mineral or synthetic, lamellate or non-lamellate. Mention may be made of talc, mica, silica, kaolin, nylon and polyethylene powders, teflon, starch, micatitanium, natural nacre, boron nitrate, microspheres such as Expancel (Nobel Industrie), polytrap (Dow Corning), and silicone resin microballs (e.g., Tospearls made by Toshiba).

The composition may further contain any additive normally employed in the cosmetic field, such as antioxidants, perfumes, essential oils, preservatives, cosmetic active ingredients, vitamins, essential fatty acids, sphingolipids, self-tanning compounds such as DHA, sunscreens, surfactants, liposoluble polymers, in particular hydrocarbonic polymers, such as polybutene, polyalkylenes, polyacrylates, and silicone polymers compatible with fatty substances. These additives may be present in the composition in a proportion of 0 to 10% by weight.

Of course, those skilled in the art will take care to select any additional compounds and/or quantities thereof, so as ensure that the advantageous properties of the composition according to the invention will not, or substantially not, be altered by the contemplated addition.

The procedures for manufacture of the compositions according to the invention do not differ in any way form the procedures conventionally used in the cosmetics field and are entirely known to the specialist. These procedures consist in mixing the different constituents of the composition, preferably after heating, then in pouring them to produce the desired shape.

The compositions according to the invention may take the form of sticks or of flexible or poured pastes, or even of an oily, potentially gelled liquid.

The compositions according to the invention may take the form of a cosmetic product, and, in particular, as a skin make-up product, especially a make-up foundation, a blusher or eyeshadow, or a lipstick.

They may also exist as uncolored products, potentially containing cosmetic active ingredients. In that case, they may be used as a lip-care base or as a fixing base to be applied on a conventional lipstick. The fixing base then forms a protective film on the lipstick film, restricts the transfer and migration thereof, and thus increases its staying power.

The compositions may also be produced as a dermatological or skin-care composition or as a sun or self-tanning composition.

The invention is illustrated in greater detail in the following examples.

EXAMPLE 1

A lipstick having the following composition was prepared:

| | |
|---|---|
| cyclopentadimethylsiloxane | 35 g |
| polyphenylmethylsiloxane | 30 g |
| silicone waxes | 10 g |
| hydrocarbonic waxes (especially polyethylene) | 10 g |
| pigments | 10 g |
| fillers (in particular, nylon powder) | 5 g |

The composition was conventionally prepared by heating the fatty substances, except for the volatile oils, at 95° and by mixing them. Next, the pigments and fillers were added, and, at 60°, the volatile oils. This mixture was mixed using a Moritz turbine at a speed of 3,000 rev./min. The mixture could then be poured into suitable molds.

In this way, a stick lipstick having a pleasant texture, which spread well and could be applied evenly, was produced. The film was comfortable to wear over time and did not migrate.

This composition was applied on the left side of the lips of several persons. As a comparison, the same composition, in which the phenylated silicone oil was replaced with a hydrocarbonic vegetable oil, was applied to the right side of the lips. The lipsticks were allowed to dry at ambient temperature for five minutes, then the lips were placed in their entirety in contact with a sheet of paper.

On all of the sheets of paper, a more marked trace of lipstick left by the composition according to prior art was found. The composition according to the invention left a very slight, barely perceptible, trace.

EXAMPLE 2

A flexible paste having the following composition was prepared:

| | |
|---|---|
| cyclopentadimethylsiloxane | 40 g |
| polyphenylmethylsiloxane (DC556 Fluid from Dow Corning) | 20 g |
| silicone wax | 10 g |
| polyethylene wax | 10 g |
| pigments | 10 g |
| fillers (in particular, nylon powder) | 5 g |

The composition was conventionally prepared by heating the fatty substances, except for the volatile oils, at 95° and by mixing them. Next, the pigments and fillers were added, and, at 60° the volatile oils. This mixture was mixed using a Moritz turbine at a speed of 3,000 rev./min. The mixture could then be poured into suitable packaging. In this way, a flexible paste having a pleasant texture, which spread well and could be applied evenly, was produced. The film was comfortable to wear over time and did not migrate.

EXAMPLE 3

A fixing base for lipstick having the following composition was prepared:

| | |
|---|---|
| cyclopentadimethylsiloxane | 35 g |
| polyphenylmethylsiloxane (DC556 Fluid from Dow Corning) | 30 g |
| silicone waxes | 10 g |
| hydrocarbonic waxes (in particular polyethylene wax) | 10 g |

The composition was prepared in accordance with Example 1.

A stick fixing base was produced. It had a pleasant texture and was easily applied on a conventional lipstick film.

What is claimed is:

1. A transfer-resistant anhydrous make-up composition in the form of a stick containing a fatty phase consisting essentially of the following substituents (i) 1–35% of phenylated silicone oil; (ii) 30–60% of volatile oil having a flashpoint of 40–100° C.; (iii) 0.5–30% of hydrocarbonic and/or silicone wax; (iv) if present, less than 5% by weight of a non-volatile hydrocarbonic oil; (v) 8 to 25% of pigments and/or nacres; and (vi) at least one other material selected from the group consisting of antioxidants, perfumes, essential oils, preservatives, cosmetic active ingredients, dermatological active ingredients, vitamins, essential fatty acids, sphingolipids, self-tanning compounds, sunscreens, surfactants, liposoluble polymers, and non-volatile silicone oils, wherein said make-up composition is resistant to transfer and/or migration and remains comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

2. The composition of claim 1, which contains less than 5% of a non-volatile hydrocarbonic oil.

3. The composition of claim 1, which does not contain a non-volatile hydrocarbonic oil.

4. The composition of claim 1, wherein the volatile oil is selected from the group consisting of cyclic or linear hydrocarbonic and silicone oils, and mixtures thereof.

5. The composition of claim 1, wherein the volatile oil is selected from the group consisting of cyclotetramethylsiloxane, cyclopentadimethylsiloxane, cyclohexadimethylsiloxane, methylhexyldimethylsiloxane, isoparafins, and mixtures thereof.

6. A transfer-resistant anhydrous make-up composition in the form of a stick containing a fatty phase consisting essentially of the following substituents (i) 1 to 35% of a phenylated silicone oil; (ii) 30 to 60% of a volatile oil having a flashpoint of 40–100° C.; (iii) 0.5 to 30% of hydrocarbonic and/or silicone wax; (iv) if present, less than 5% by weight of a non-volatile hydrocarbonic oil; (v) 8 to 25% of pigments and/or nacres; and (vi) at least one other material selected from the group consisting of antioxidants, perfumes, essential oils, preservatives, cosmetic active ingredients, dermatological active ingredients, vitamins, essential fatty acids, sphingolipids, self-tanning compounds, sunscreens, surfactants, liposoluble polymers, and non-volatile silicone oils, wherein the phenylated silicone oil is selected from oils having formula (I) and mixtures thereof:

(I)

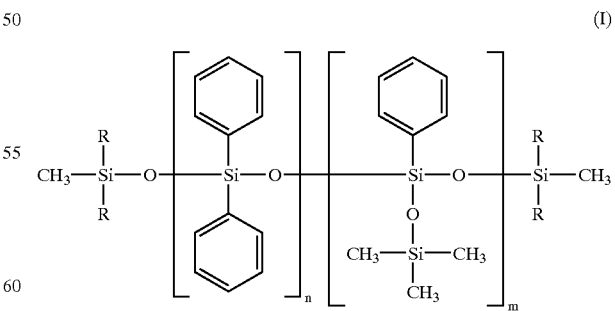

wherein R is an alkyl radical having 1 to 30 carbons, an aryl radical, or an aralkyl radical; n is a whole number ranging from between 0 and 100; and m is a whole number ranging between 0 and 100, with the proviso that the sum of m+n ranges between 1 and 100, wherein said composition is resistant to transfer and/or migration and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

7. The composition according to claim 6, wherein the phenylated silicone oil is selected from the group consisting of oils corresponding to Formula (I), wherein R is selected from the group consisting of methyl, ethyl, propyl, isopropyl, decyl, dodecyl, octadecyl, phenyl, tolyl, benzyl, and phenethyl radicals.

8. A transfer-resistant anhydrous make-up composition in the form of a stick containing a fatty phase consisting essentially of the following substituents (i) 20 to 30% of a phenylated silicone oil; (ii) 30 to 60% of a volatile oil having a flash point of 40–100° C.; (iii) 0.5 to 30% of hydrocarbonic and/or silicone wax; (iv) if present, less than 5% by weight of a non-volatile hydrocarbonic oil; (v) 8 to 25% of pigments and/or nacres; and (vi) at least one other material selected from the group consisting of antioxidants, perfumes, essential oils, preservatives, cosmetic active ingredients, dermatological active ingredients, vitamins, essential fatty acids, sphingolipids, self-tanning compounds, sunscreens, surfactants, liposoluble polymers, and non-volatile silicone oils, wherein said composition is resistant to transfer and/or migrated and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

9. The make-up composition of claim 1, which is selected from the group consisting of foundations, blushers, eyeshadows, lipsticks, lip care or lip fixing bases, skin care products, sunscreens, and self-tanning compositions.

10. The composition according to claim 1, which comprises 10–20% by weight of hydrocarbonic wax and 0–10% by weight of silicone wax.

11. The composition according to claim 1, which further comprises a particulate phase present in a proportion ranging from 0–35% by weight.

12. The composition according to claim 1, wherein said particulate phase is present in a proportion ranging from 5–25% by weight.

13. The make-up composition of claim 1, which yields a homogeneous film upon application which film is resistant to transferal or migration after application to skin, semi-mucous membrane membranes or mucous membranes.

14. A make-up composition according to claim 6, which is selected from the group consisting of foundations, blushers, eye shadows, lipsticks, lip care or lip-fixing bases, skin care products, sunscreens and self-tanning compositions.

15. A make-up composition according to claim 7, which is selected from the group consisting of foundations, blushers, eye shadows, lipsticks, lip care or lip-fixing bases, skin care products, sunscreens and self-tanning compositions.

16. The make-up composition according to claim 14, which comprises 10–20% by weight of hydrocarbonic wax and 0–10% by weight of silicone wax.

17. The make-up composition according to claim 15, which comprises 10–20% by weight of hydrocarbonic wax and 0–10% by weight of silicone wax.

18. A transfer-resistant anhydrous make-up composition in the form of a stick consisting essentially of a fatty phase consisting essentially of the following substituents (i) 1 to 35% of a phenylated silicone oil; (ii) 30 to 60% of a volatile oil having a flash point of 40–100° C.; (iii) 0.5 to 30% of hydrocarbonic and/or silicone wax; (iv) if present, less than 20% by weight of a non-volatile hydrocarbonic oil; and (v) at least one other material selected from the group consisting of antioxidants, perfumes, essential oils, preservatives, cosmetic active ingredients, dermatological active ingredients, vitamins, essential fatty acids, sphingolipids, self-tanning compounds, sunscreens, surfactants, liposoluble polymers, and non-volatile silicone oils, wherein said composition is resistant to transfer and/or migration and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

19. A transfer-resistant anhydrous make-up composition in the form of a stick containing, in a fatty phase, the following substituents (i) 1–35% of phenylated silicone oil; (ii) 30–60% of volatile oil having a flashpoint of 40–100° C.; (iii) 0.5–30% of hydrocarbonic and/or silicone wax; (iv) if present, less than 5% by weight of a non-volatile hydrocarbonic oil; and (v) 8 to 25% of pigments and/or nacres, and wherein said fatty phase does not comprise a silicone resin having an esterified chain comprising at least twelve carbon atoms, and further wherein said make-up composition is resistant to transfer and/or migration and remains comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

20. A transfer-resistant anhydrous make-up composition in the form of a stick containing, in a fatty phase, the following substituents (i) 1 to 35% of a phenylated silicone oil; (ii) 30 to 60% of a volatile oil having a flashpoint of 40–100° C.; (iii) 0.5 to 30% of hydrocarbonic and/or silicone wax; (iv) if present, less than 5% by weight of a non-volatile hydrocarbonic oil; and (v) 8 to 25% of pigments and/or nacres, and wherein said fatty phase does not comprise a silicone resin having an esterified chain comprising at least twelve carbon atoms, and further wherein the phenylated silicone oil is selected from oils having formula (I) and mixtures thereof:

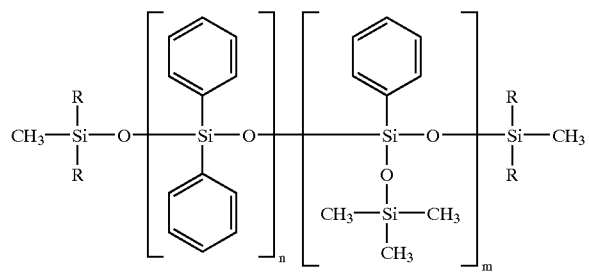

(I)

wherein R is an alkyl radical having 1 to 30 carbons, an aryl radical, or an aralkyl radical; n is a whole number ranging from between 0 and 100; and m is a whole number ranging between 0 and 100, with the proviso that the sum of m+n ranges between 1 and 100, wherein said composition is resistant to transfer and/or migration and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

21. A transfer-resistant anhydrous make-up composition in the form of a stick containing, in a fatty phase, the following substituents (i) 20–30% of a phenylated silicone oil; (ii) 30 to 60% of a volatile oil having a flash point of 40–100° C.; (iii) 0.5 to 30% of hydrocarbonic and/or silicone wax; (iv) if present, less than 5% by weight of a non-volatile hydrocarbonic oil; and (v) 8 to 25% of pigments and/or nacres, and wherein said fatty phase does not comprise a silicone resin having an esterified chain comprising at least twelve carbon atoms, and further wherein said composition is resistant to transfer and/or migrated and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

22. A transfer-resistant anhydrous make-up composition in the form of a stick consisting essentially of, in a fatty phase, the following substituents (i) 20 to 30% of a phenylated silicone oil; (ii) 30 to 60% of a volatile oil; (iii) 0.5 to 30% of hydrocarbonic and/or silicone wax; and (iv) if present, less than 20% by weight of a non-volatile hydrocarbonic oil, and wherein said fatty phase does not comprise a silicone resin having an esterified chain comprising at least twelve carbon atoms, and further wherein said composition is resistant to transfer and/or migration and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified as (i) through (iv).

23. The transfer-resistant anhydrous make-up composition of claim 1 wherein said fatty acid phase is a flexible, molded paste.

24. The transfer-resistant anhydrous make-up composition of claim 1 wherein said fatty acid phase is an oily gelled liquid.

25. A transfer-resistant anhydrous make-up composition in the form of a stick consisting essentially of a fatty phase consisting essentially of the following substituents (i) 20 to 30% of a phenylated silicone oil; (ii) 30 to 60% of a volatile oil; (iii) 0.5 to 30% of hydrocarbonic and/or silicone wax; (iv) if present, less than 20% by weight of a non-volatile hydrocarbonic oil; (v) 8 to 15% of pigments; and (vi) at least one other material selected from the group consisting of antioxidants, perfumes, essential oils, preservatives, cosmetic active ingredients, dermatological active ingredients, vitamins, essential fatty acids, sphingolipids, self-tanning compounds, sunscreens, surfactants, liposoluble polymers, and non-volatile silicone oils, wherein said composition is resistant to transfer and/or migration and is comfortable to a user after topical application, wherein comfortable to a user means that said composition exhibits at least one of the following properties: (1) that the subject composition does not elicit a tugging sensation; or (2) that it does not cause drying of the lips or the skin upon topical application, and wherein the transfer-resistant properties of said composition are attributable only to the essential substituents identified in (i) through (iv).

* * * * *